United States Patent
Wegener

(10) Patent No.: US 12,303,671 B2
(45) Date of Patent: May 20, 2025

(54) SYRINGE WITH SYRINGE CLOSURE

(71) Applicant: Fenwal, Inc., Lake Zurich, IL (US)

(72) Inventor: Christopher J. Wegener, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 311 days.

(21) Appl. No.: 17/466,083

(22) Filed: Sep. 3, 2021

(65) Prior Publication Data

US 2022/0072234 A1   Mar. 10, 2022

Related U.S. Application Data

(60) Provisional application No. 63/076,843, filed on Sep. 10, 2020.

(51) Int. Cl.
| | |
|---|---|
| *A61M 5/00* | (2006.01) |
| *A61M 5/31* | (2006.01) |
| *A61M 5/315* | (2006.01) |
| *A61M 5/32* | (2006.01) |

(52) U.S. Cl.
CPC ...... *A61M 5/31501* (2013.01); *A61M 5/3145* (2013.01); *A61M 5/3202* (2013.01); *A61M 2005/3109* (2013.01); *A61M 2005/3123* (2013.01)

(58) Field of Classification Search
CPC .......... A61M 25/0054; A61M 5/14526; B65D 39/0095; B65D 39/0082
See application file for complete search history.

(56) References Cited

U.S. PATENT DOCUMENTS

| | | | | |
|---|---|---|---|---|
| 2,186,987 A | * | 1/1940 | Nesset | A61M 5/165 210/453 |
| 2,372,227 A | * | 3/1945 | Sanford | B65D 41/0442 220/304 |
| 4,231,494 A | * | 11/1980 | Greenwood | G01F 11/00 222/394 |
| 4,251,003 A | * | 2/1981 | Bodenmann | B65D 55/02 215/254 |
| 5,019,037 A | * | 5/1991 | Wang | A61F 9/00727 604/23 |

(Continued)

FOREIGN PATENT DOCUMENTS

| | | | | |
|---|---|---|---|---|
| EP | 3329947 A2 | * | 6/2018 | ............ A61J 1/2003 |
| EP | 3669910 A1 | * | 6/2020 | |
| WO | WO-2018065880 A1 | * | 4/2018 | ........ A61M 5/14526 |

OTHER PUBLICATIONS

Extended European Search Report for EP 21192150.7 dated Jan. 4, 2022; 9 pages.

*Primary Examiner* — William R Carpenter
(74) *Attorney, Agent, or Firm* — Cook Alex Ltd.

(57) ABSTRACT

A syringe including a barrel, a plunger, and a vented closure. The barrel has a bore, and an end with an opening in communication with the bore and a barrel flange disposed outwardly of the opening. The plunger is disposed in the bore, and is movable along the bore. The vented closure is attached to the barrel at the end, and includes a stopper, a cap and a filter. The stopper is disposed over and/or in the opening in communication with the bore. The cap includes a body disposed over the stopper, and a fastener engaged with the barrel flange. The filter is disposed between the stopper and the cap, or in at least one of the stopper and the cap.

13 Claims, 8 Drawing Sheets

(56) References Cited

U.S. PATENT DOCUMENTS

| | | | | |
|---|---|---|---|---|
| 5,165,560 | A * | 11/1992 | Ennis, III | B65D 51/002 |
| | | | | 215/274 |
| 5,873,499 | A * | 2/1999 | Leschinsky | A61M 5/31593 |
| | | | | 222/391 |
| 5,887,764 | A * | 3/1999 | Ennis, III | B05C 17/015 |
| | | | | 222/386 |
| 6,296,625 | B1 * | 10/2001 | Vetter | A61M 5/3135 |
| | | | | 604/227 |
| 6,663,601 | B2 | 12/2003 | Hetzler et al. | |
| 7,810,529 | B2 * | 10/2010 | Py | B65B 7/161 |
| | | | | 141/82 |
| 2012/0232524 | A1 * | 9/2012 | Hyun | A61J 15/00 |
| | | | | 604/126 |
| 2014/0263403 | A1 * | 9/2014 | Conner | B05C 11/1034 |
| | | | | 222/386 |
| 2014/0276415 | A1 * | 9/2014 | Davis | A61M 39/20 |
| | | | | 604/150 |
| 2016/0081849 | A1 * | 3/2016 | Tsai | A61M 5/3137 |
| | | | | 604/290 |
| 2016/0175529 | A1 | 6/2016 | Hyun et al. | |
| 2016/0243309 | A1 * | 8/2016 | Cupicha | A61M 5/31511 |
| 2020/0039698 | A1 * | 2/2020 | Ikushima | B65D 41/28 |
| 2020/0197942 | A1 | 6/2020 | Wegener et al. | |

* cited by examiner

SYRINGE WITH SYRINGE CLOSURE

CROSS-REFERENCE TO RELATED APPLICATIONS

This application claims the benefit of U.S. Provisional Application No. 63/076,843, filed Sep. 10, 2020, which is hereby incorporated herein by reference.

TECHNICAL FIELD

The present disclosure is generally directed to a closure for a syringe. More particularly, the present disclosure is directed to a closure for a syringe intended to interface with a pneumatic driving system, or driver, and to provide a seal over a range of temperatures.

BACKGROUND

A new class of medicines is gaining much attention. This class of medicines employs functional cells for disease treatment. These medicines, either autologous or allogenic in nature, present certain challenges for therapy manufacturers or providers, however.

From a historical standpoint, cell-based therapies most commonly have been delivered from flexible plastic containers, or bags. With most cell-based therapeutics requiring cryopreservation at liquid nitrogen temperatures to preserve cell function during shipping or patient preparations regimens, bags present several challenges. The bags can be fragile when frozen, and are susceptible to breakage and/or contamination. In addition, fluids held up in the bag can prevent incomplete dosing.

In the alternative, vials have been considered. Vials are generally easy to handle and can be compatible with cryopreservation. The filling of vials is considered an "open" manipulation, however, and carries increased risk of drug product contamination, especially for small lot drugs that would require hand-filling. Thus, vials are not a complete answer.

Prefilled syringes are another option, in the form of a delivery vessel that is ready-to-use. However, the designs of conventional syringes do not allow them to maintain closure during cryopreservation.

It would be desirable to provide a container that overcame, at least in part, the disadvantages of conventional containers for use with cell-based medicines.

SUMMARY

In an aspect, a syringe includes a barrel, a plunger, and a vented closure. The barrel has a bore, and an end with an opening in communication with the bore and a barrel flange disposed outwardly of the opening. The plunger is disposed in the bore, and is movable along the bore. The vented closure is attached to the barrel at the end, and includes a stopper, a cap and a filter. The stopper is disposed over and/or in the opening in communication with the bore. The cap includes a body disposed over the stopper, and a fastener engaged with the barrel flange. The filter is disposed between the stopper and the cap, or in at least one of the stopper and the cap.

DETAILED DESCRIPTION

Figure 1:
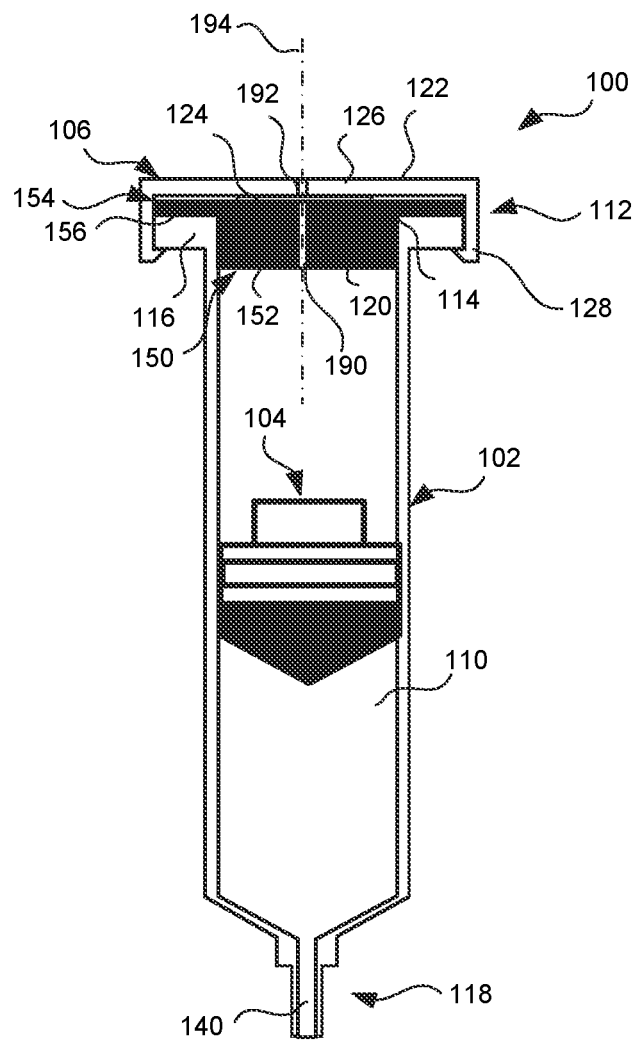
FIG. 1 is a partial cross-sectional view of a syringe with syringe closure according to an embodiment.

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Furthermore, while certain relative spatial terms, such as left, right, upper, lower, inner and outer, have been used relative to the embodiments as illustrated in the drawings, these terms have been used for ease of explanation relative to those particular illustrations. The terms are not intended to require a particular orientation of the syringe and closure in use. Other relative spatial terms might be substituted for those used in the text if the embodiments were illustrated in a different orientation on the page, as will be recognized by the reader.

Starting with reference to FIG. 1, a syringe 100 includes a barrel 102, a plunger 104, and a vented closure 106. The syringe 100 according to these embodiments may be used to contain, for example, a cell-based medicine, and may be adapted to store that medicine at a variety of temperatures. Moreover, the syringe 100 may provide a container that is a ready-to-use delivery vessel, pre-filled syringes 100 being used alone or as a component of an autoinjector or autoinfuser. In addition, the syringe 100 described herein may be used with pneumatic driving system, or drivers, to reduce the risks of contamination during filling.

The barrel 102 of the syringe 100 has a bore 110. The barrel 102 also has a first end 112 with an opening 114 in communication with the bore 110, and a barrel flange 116 disposed outwardly of the opening 114. The plunger 104 is disposed in the bore 110, and is movable along the bore 110, for example between the first end 112 and a second end 118.

The vented closure 106 is attached to the barrel 102 at the first end 112 (via a snap-fit, for example), and includes a stopper 120, a cap 122 and a filter 124. The stopper 120 is disposed over and/or in the opening 114 in communication with the bore 110. The cap 122 includes a body 126 disposed over the stopper 120, and a fastener 128 engaged with the barrel flange 116. The filter 124 is disposed between the stopper 120 and the cap 122, or in at least one of the stopper 120 and the cap 122. While the cap 122 appears spaced from the stopper 120 by the width of the filter 124, this is an exaggeration for purposes of illustration of each of the parts—in actuality the cap 122 may abut the stopper 120 as well as the filter 124.

Figure 5:
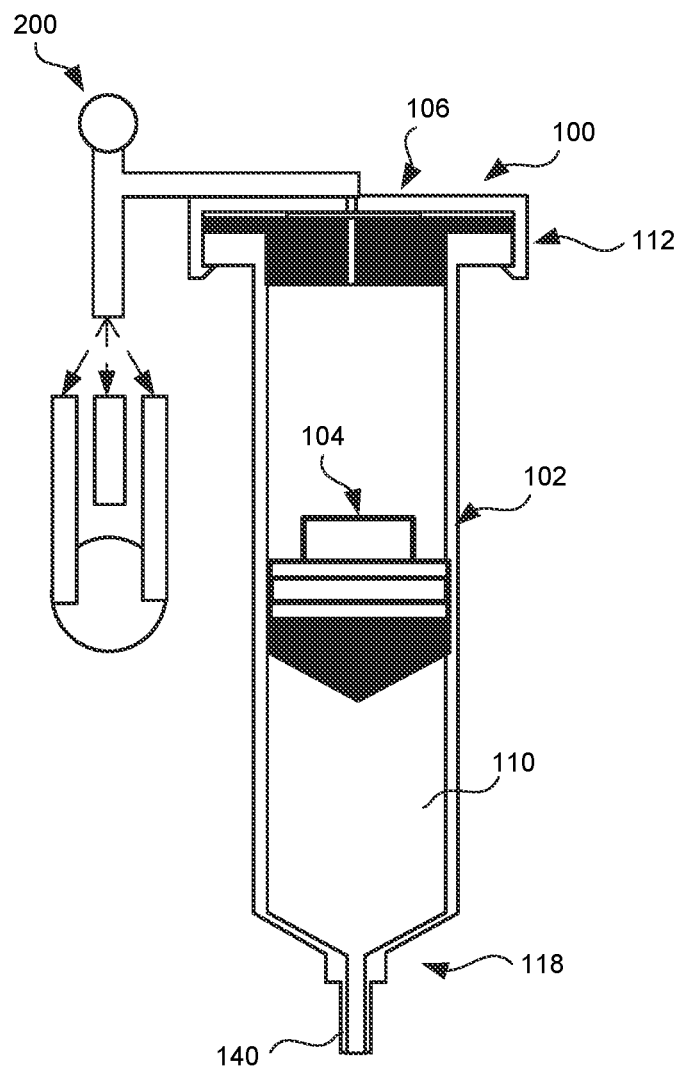
FIG. 5 is a schematic view of the syringe with syringe closure of FIG. 1 in combination with a pneumatic driving system, or driver.

The vented closure 106 permits a pneumatic driver to be attached to the syringe 100 to move the plunger 104 along the bore 110. See FIG. 5. Because only filtered gas (e.g., air) enters and exits the bore 110 to move the plunger 104, the possible contamination risks that might be related to the use of a mechanical driver (including plunger handle and linear actuator) entering the bore through an open end can be eliminated. Further, the stopper 120 provides a further seal useful under cryopreservation conditions, thereby reducing the role that the plunger 104 has to play under such conditions in sealing the bore 110. Further, where the closure 106 is removeable, the syringe 100 represents an easily configurable, ready-to-use delivery vessel.

Having discussed the syringe 100 in general terms, the details of the syringe 100 are discussed, as well as some of its uses.

As mentioned above with reference to FIG. 1, the barrel 102 has a first end 112, the first end 112 including the opening 114 and the barrel flange 116, and a second end 118 located at the opposite end of the barrel 102. According to the illustrated embodiment, the barrel 102 may have a tip 140 at the second end 118, the tip 140 being in fluid communication with the bore 110. The tip 140 may be configured to connect to a needle, for example as a luer lock or a luer slip tip. Alternatively, the tip 140 may include a septum that will be pierced by a cannula that is attached to or is part of a delivery system, such as may be found in an autoinjector or autoinfuser device. The tip 140 may be closed with a cap or cover (not shown) in storage, or when not in use.

According to certain embodiments, the tip 140 may be connected to tubing, and define a processing set that may be used with other equipment. In fact, more than one syringe 100 may be attached to such tubing to define the processing set. When the syringe 100 is pre-connected to tubing in such a processing set, the syringe can be terminally sterilized, further reducing the chances of contamination when processed cells or other material is transferred into and out of the syringe 100.

At the first end 112, the barrel flange 116 may depend outwardly from the barrel 102, but may not depend radially outwardly from the barrel 102 to the same distance in all directions. See, e.g., FIG. 2. That is, the barrel flange 116 may not form an annular shelf depending from the barrel in a cantilevered fashion, but instead may be in the form of two opposite cantilevered structures that depend from the barrel 102 from opposite sides (e.g., left and right) of the barrel 102. These structures may be used during delivery of the medicine from the syringe 100, by placing the index and middle fingers against the flange 116 while depressing on a plunger handle that is attached to the plunger 104. In other variants, the barrel flange 116 may be too narrow to be used in this fashion, with index and middle fingers disposed against the flange 116.

Figure 6A:
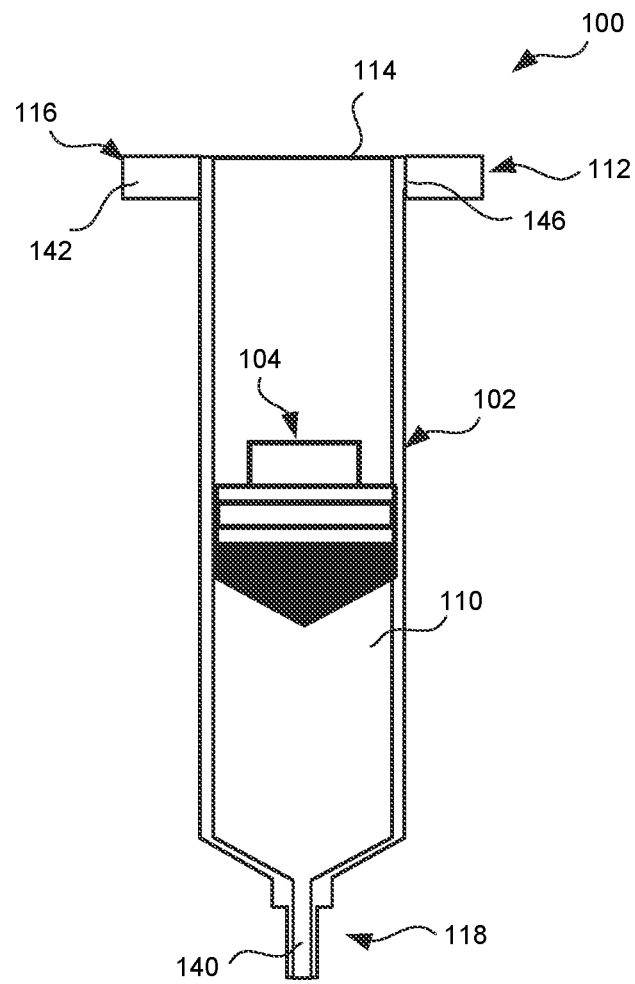
FIG. 6A is a partial cross-section view of another embodiment of a syringe for use with a syringe closure according to the embodiments disclosed herein.
Figure 6B:
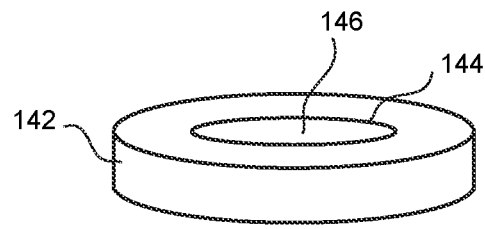
FIG. 6B is a perspective view of a collar used in the syringe of FIG. 6A to form or define a barrel flange.

According to still other embodiments, the barrel flange 116 may not be formed as a single structure with the barrel 102 (i.e., an integral or unitary structure). One such alternate embodiment is illustrated in FIGS. 6A and 6B. As illustrated in FIG. 6A, the barrel 102 may have a slight taper between the first end 112 and the second end 118, and an annular structure, referred to herein as a collar 142, may be positioned on the barrel 102 to define the barrel flange 116. See FIG. 6B. In particular, the collar 142 has an opening 144 that connects to a passage 146 formed therethrough, and the barrel 102 is disposed into the opening 144 and through the passage 146 as the collar 142 is moved along the barrel 102 from the second end 118 to the first end 112. The collar 142 may be held in place at the first end of the barrel 102 by the taper of the barrel 102 and a friction-fit of the collar 142 and the barrel 102. According to other embodiments, the barrel 102 may not have a taper, and the collar 142 may be held in place by friction-fit alone. According to still other embodiments, the collar 142 may be joined to the barrel 102 using conventional joining methods.

In addition, while the illustrated embodiments may disclose a single barrel flange 116, according to other embodiments, more than one flange may be disposed along the barrel 102. For example, there may be a first barrel flange formed integrally with the barrel 102, and a second barrel flange that is formed or defined by a collar, like the collar 142, that is disposed along the barrel 102. The closure 106 may cooperate with one or more of these barrel flanges 116.

The barrel 102, including the flange 116, may be formed of any of a number of different plastics. For example, the barrel 102 and the flange 116 may be made from a cyclic olefin polymer or copolymer. It is believed that such a polymer may provide suitable performance over a range of temperatures, including those that the syringe 100 may experience during cryopreservation. In addition, where the flange 116 is not formed integrally with the barrel 102, the two structures may be made of different plastics.

The design of the plunger 104 and the materials used in its manufacture may vary. In fact, because of the closure 106, and in particular the stopper 120 being present to seal, at least in part, the bore 110, the design of the plunger 104 and the material selection may be even more varied because it is not necessary to design the plunger 104 to provide a complete seal even under cryopreservation conditions. This permits the plunger 104 to be designed to optimize for (or at least emphasize) other issues, such as deliverability, instead of having to trade off performance relative to storage capability over a wide range of temperatures.

Figure 2:
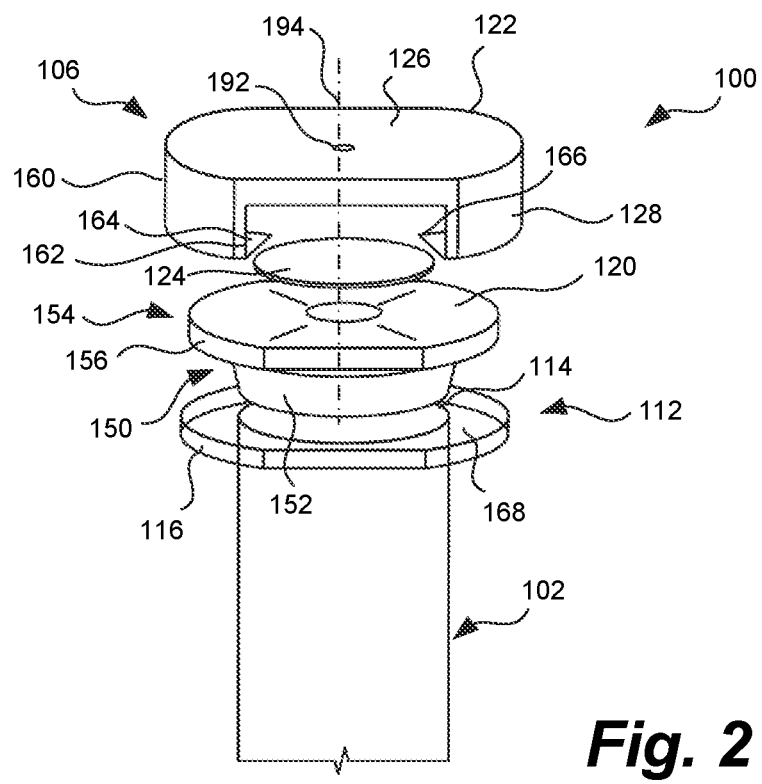
FIG. 2 is a partial, enlarged, exploded view of the syringe with syringe closure of FIG. 1.
Figure 3:
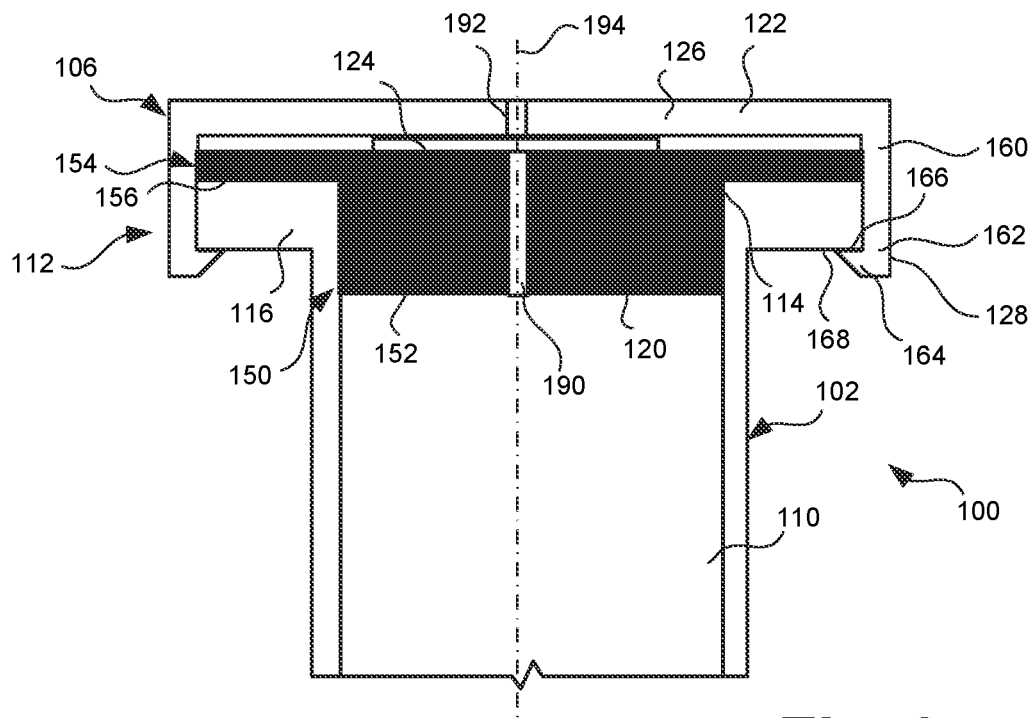
FIG. 3 is a partial, enlarged, cross-sectional view of the syringe with syringe closure of FIG. 1.

Returning then to the closure 106 and FIGS. 1-3, the embodiment of the stopper 120 illustrated not only covers the opening 114, it is also disposed within the bore 110 of the barrel 102. That is, the stopper 120 includes a first end 150 in the form of a plug 152 that is disposed within the bore 110, and a second end 154 that has a stopper flange 156 that depends therefrom outside the bore 110 and over the opening 114. The plug 152 may have a cross-section that is substantially similar to the cross-section of the bore 110; for example, where the bore 110 is cylindrical, the plug 152 may be cylindrical. Similarly, the stopper flange 156 may have a shape that is complementary to the shape of the barrel flange 116; for example the stopper flange 156 may include cantilevered structures (or wings) that depend from opposite sides (e.g., left and right) from the stopper 120. According to other embodiments, the stopper 120 may be disposed only over the opening 114, or may be disposed only within the bore 110.

The stopper 120 may be maintained in place in part because of the presence of the plug 152 in the bore 110. In fact, an outer surface of the plug 152 facing an inner surface of the bore 110 may have structures (such as ribs) that cooperate with the inner surface of the bore 110 to prevent material from passing between the outer surface of the plug 152 and the inner surface of the bore 110 and to improve the securement of the plug 152 in the bore 110. The stopper 120 is also maintained in place as a consequence of the cooperation of the cap 122 with the stopper 120, an in particular the cap 122 with the stopper flange 156.

As illustrated, the body 126 of the cap 122 overlies the stopper flange 156. According to certain embodiments, the body 126 may be shaped to be complementary to the shape of the stopper flange 156, so that the body 126 is coextensive with the periphery of the stopper flange 156. See FIG. 2. According to other embodiments, the body of the cap 122 may overlie only those regions of the stopper flange 156 that also overlie the barrel flange 116. For example, the body of the cap 122 may include a relatively large opening, such that the regions of the body 126 of the cap 122 that overlie the flange 156 are connected with a web of material, but the cap 122 is still considered to secure the stopper flange 156 between the body 126 of the cap 122 and the barrel flange 116.

The cap 122 also includes the fastener 128, and the fastener 128 may take a variety of shapes as is reflected in the alternative embodiments discussed later. Many embodiments of the fastener 128 are configured to cooperate or engage, directly or indirectly, with a surface of the barrel flange 116 to secure the stopper 120 to the barrel 102. That is, the fastener 128 may have a feature (e.g., a barb) that it is disposed directly against the surface of the barrel flange 116 to secure the stopper 120 to the barrel 102. Alternatively, the fastener 128 may include an intermediate structure (e.g., a collar, similar to the collar 142 introduced above) that is disposed directly against the surface of the barrel flange 116, and then the fastener 128 may include a feature (e.g., a barb) that is disposed directly against a surface of the intermediate structure (e.g., collar) to secure the stopper 120 to the barrel 102.

According to the illustrated embodiment of FIGS. 1-5, and with particular reference to FIGS. 2 and 3, the fastener 128 includes a skirt 160 that depends from the body 126, at least those regions that overlie the barrel flange 116, the skirt 160 having one or more barbs 162 depending therefrom. The barb(s) 162 cooperated with the barrel flange 116 to secure the stopper in place, and may also cause the cap 122 to compress the stopper 120 to create a hermetic static seal in the bore 110, which hermetic seal may be compatible with room temperature, refrigeration, and cryogenic storage.

According to the illustrated embodiment, the cap 122 includes a skirt 160 that depends downwardly from the body 126. It will be recognized that directional references are adopted herein for the convenience of the reader, such that downward does not place an absolute limitation on the nature of the skirt 160. Instead, it is meant to convey that the skirt 160 depends from the cap 122 in a direction toward the barrel flange 116, considering that the cap 122 previously been described as disposed over the stopper flange 156, which in turn overlies the barrel flange 116.

The skirt 160 is not continuous about the perimeter of the body 126 of the cap 122, although it could be according to certain embodiments. Instead the skirt 160 includes two sections, each of which borders the sections of the body 126 the overlie the barrel flange 116. This skirt 160 could, in other embodiments, be divided even further, so as to define a plurality of skirt sections, or fingers. In the same fashion that the barb 162 is defined along the perimeter of the skirt sections 160 illustrated, each of these fingers could have a barb disposed at a downward end thereof, each barb cooperating with the barrel flange 116. Such an arrangement may provide for a more flexible skirt 160 overall, making separation of the closure 106 from the barrel 102 easier.

As mentioned above, the barb 162 engages the barrel flange 116 to secure the closer 106 to the barrel 102. It will be recognized that the barb 162 may have a head 164 with an inner surface 166, and the barrel flange 116 may have an outer surface 168. See FIG. 3. In considerable of the spatial directions being used elsewhere for ease of explanation, the surface 166 may be referred to as facing upward, while the surface 168 may be referred to as facing downward. The surfaces 166, 168 abut each other with the stopper 120 and cap 122 arranged on the barrel 102 as illustrated.

According to embodiments such as the illustrated embodiment, the engagement of the surfaces 166, 168 is the primary attachment mechanism between the barrel 102 and the snap-fit closure 106, such that with sufficient force applied to the closure 106, the closure 106 may be separated from the barrel 102. The closure 106 may be referred to as removable even if the force applied causes permanent deformation, or even failure, of the cap 122 (and in particular the skirt 160). In fact, according to certain embodiments, the skirt 160 and/or barbs 162 may be separated from the cap 122 to permit the closure 106 to be removed from the barrel 102. According to such an embodiments, a rupturable boundary (e.g., a line of weakness in the material) may be formed between the skirt 160 and/or barbs 162 and the remainder of the cap 122, thereby permitting the skirt and/or barbs 162 to be separated from the remainder of the cap 122 with peeling or tearing of the material along the rupturable boundary. The skirt 160 and/or barbs 162 also may be removable after separation. On the other hand, the closure 106 may be referred to as reversibly removeable if the force required may cause the cap 122 to separate causes the cap 122, and in particular the skirt 160, to deflect or flex, but is not sufficient to cause permanent deformation or failure.

Figure 4:
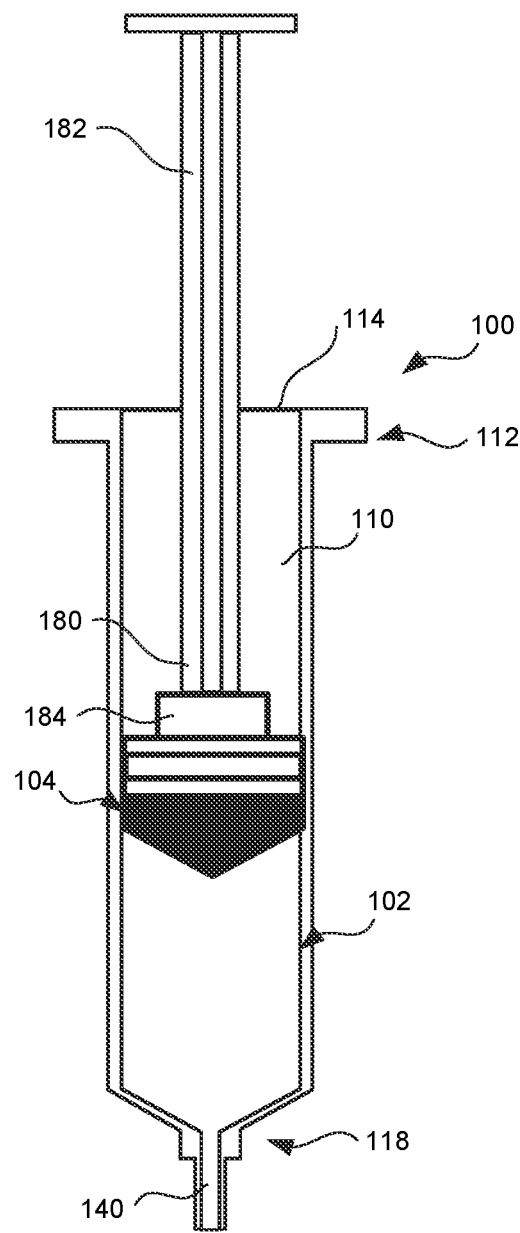
FIG. 4 is a partial cross-sectional view of the syringe with syringe closure of FIG. 1 in combination with a plunger handle.

The closure 106 may be removeable so that, after filling, a mechanical control mechanism can cooperate with the plunger 104 directly. That is, the closure 106 is designed to permit gas (e.g., air) to move the plunger 104 along the bore 110. However, while a pneumatic system may be used during filling to move the plunger 104, a large number of delivery systems use mechanical control mechanisms instead of gaseous ones. For example as illustrated in FIG. 4, the closure 106 may be removed so that a first end 180 of a plunger handle 182 may be disposed through the opening 114 and into the bore 110. The plunger 104 may have an attachment mechanism 184 formed therein or on a surface thereof that cooperates with the plunger handle 182, for example the first end 180. According to an embodiment, the first end 180 may have a thread formed thereon, and the plunger 104 may have a threaded bore formed therein, the first end 180 capable of being attached to the plunger 104 by screwing the first end 180 into the threaded bore 184 of the plunger 104.

As mentioned generally above, the closure 106 is vented, which venting permits the syringe 100 to be used with a pneumatic driver during filing, and perhaps also with a gaseous driver as part of a delivery system. To this end, the stopper 120 and the body 126 of the cap 122 each have at least one through-lumen 190, 192 according to the illustrated embodiment. See FIGS. 1 and 3. As is also illustrated, the through-lumens 190, 192 of the stopper 120 and cap 122 are aligned along a common longitudinal axis 194, which axis 194 happens to be central axis of the syringe 100 as well. The filter 124 is disposed between the body 126 of the cap 122 and the stopper 120 along the axis 194, and thus between the through lumen 190 of the stopper 120 and the through-lumen 192 of the cap 122. The filter 124 may be made of filter media that can filter particle as small as 0.22 microns.

In addition to capturing the filter 124 between the stopper 120 and the cap 122, the filter 124 may be joined to either the stopper 120 or the cap 122. For example, the filter 124 may be irreversibly joined to either the stopper 120 or the cap 122 through the use of adhesives, or common plastic joining techniques. These techniques may include spin welding, hot plate welding, radio-frequency (RF) welding, and laser welding, for example, and may be selected based on the materials used for the stopper 120 or cap 122 and the filter 124.

According to other embodiments, the filter 124 may be embedded in the stopper 120 or the cap 122. According to such an embodiment, the filter 124 may be in one of the through-lumens 190, 192, for example, but still at the junction between the through-lumens 190, 192. According to still other embodiments, the filter 124 may be disposed not between the through-lumens 190, 192, but at an inner end of the through-lumen 190 or an outer end of the through lumen 192. Further alternative arrangements are also possible.

The closure 106 may be used with a pneumatic driver, as mentioned above. The closure 106 may be connected to the pneumatic driver, such as the driver 200 illustrated in FIG. 5. It will be recognized that the pneumatic driver 200 may be in the form of a pneumatic pump, for example, and may be capable of coupling pressure, vacuum or vent to the syringe 100. As an alternative, the pneumatic driver may include a combination of valves and pressurized reservoirs.

It will be recognized that while an embodiment of the syringe 100 with closure 106 has been illustrated in FIGS. 1-5, other embodiments are possible, as illustrated in FIGS. 7A-B, 8A-B, 9A-B. The same numbering scheme has been used for the features of the syringe 100, with the caveat that the above discussion as to variants of the syringe 100 (e.g., with reference to FIG. 6) applies with equal force to these additional embodiments. A numbering scheme where structures of the closure of FIGS. 7A-B, 8A-B, 9A-B similar to those of the closure 106 have been numbered in a similar, but not identical, fashion has been adopted for readability.

Figure 7A:
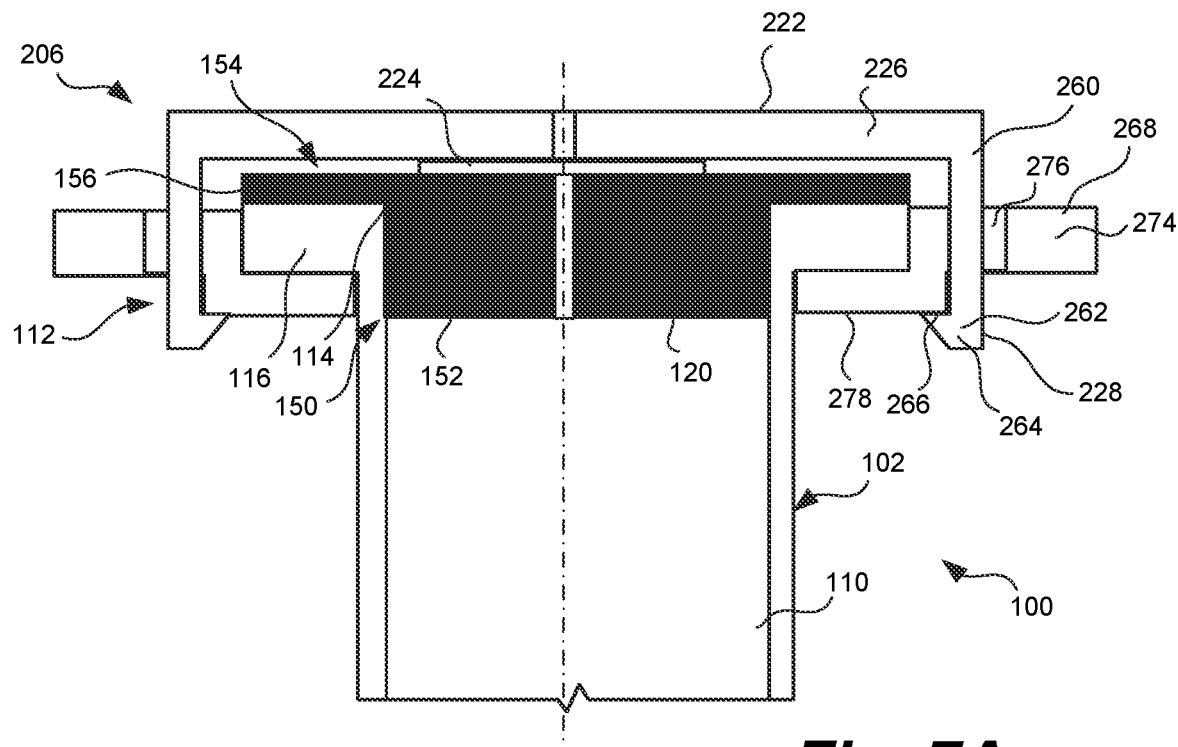
FIG. 7A is a partial, enlarged, cross-sectional view of a syringe with syringe closure according to another embodiment.
Figure 7B:
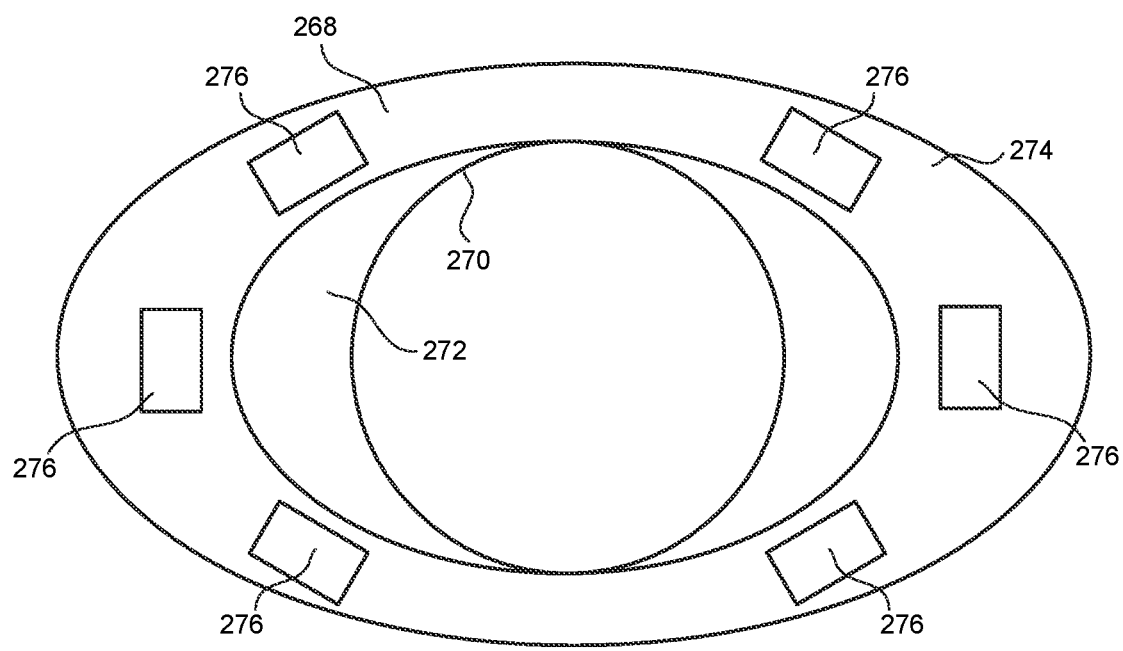
FIG. 7B is a plan view of a collar used in the embodiment of FIG. 7A.

FIGS. 7A and 7B illustrate a vented closure 206 that is attached to the barrel 102 of the syringe 100 at the first end 112. The vented closure 206 includes a stopper 120, a cap 222, and a filter 224. As in the embodiment of FIGS. 1-5, the stopper 120 is disposed over and in the opening 114 in communication with the bore 110. The cap 222 includes a body 226 disposed over the stopper 120, and a fastener 228 engaged with the barrel flange 116. The filter 224 is illustrated as disposed between the stopper 120 and the cap 222.

The embodiment of the cap 222 of FIGS. 7A and 7B differs from that of the embodiment of the cap 122 of FIGS. 1-5 in that the fastener 228 does not directly engage the barrel flange 116. Instead, the cap 222 engages an intermediate structure that is disposed between the cap 222 and the barrel flange 116, with surfaces of the cap 222 and the intermediate structure abutting (i.e. in direct contact) and surfaces of the intermediate structure and the barrel flange 116 abutting.

The cap 222 includes a skirt 260 having a plurality of spaced barbs 262, each of the barbs 262 being supported separately about the periphery of the cap 222. Each of the barbs 262 has a head 264 with an inner surface 266, which has a function similar to the surface 166 of the barb 162 of the cap 122. The closure 206 also includes the aforementioned intermediate structure, or collar, 268, which cooperates with the cap 222, and in particular the barbs 262, to secure the cap 222 to the barrel 102 of the syringe 100.

The collar 268 has a passage 270, through which the barrel 102 of the syringe 100 is received when the collar 268 is disposed on the barrel 102. Similar to the collar 142, the barrel 102 may be disposed in the passage 270 as the collar 268 is moved from the second end 118 to the first end 112. The movement of the collar 268 may be halted at the first end 112 by the barrel flange 116, when a surface of the collar 268 abuts the barrel flange 116. According to the illustrated embodiment, the collar 268 may have a recess 272 formed in an upper surface thereof to receive the barrel flange when an upper surface of the collar 268 abuts the barrel flange 116.

The collar 268 also has a rim 274 disposed radially outward from the passage 270, and from the recess 272. The rim 274 has a plurality of apertures 276 disposed about the periphery of the rim 274. As illustrated, there are six apertures 276, although according to other embodiments there may be a greater number or a lesser number of apertures 276. The apertures 276 are spaced from each other in a pattern that is a mirror image about at least one axis, although again that need not be the case according to all embodiments.

The apertures 276 are formed through the collar 268, such that the barbs 262 are received through the apertures 276, and abut an outer surface 278 of the collar 268 to secure the cap 222 to the barrel flange 116. In particular, the surface of the recess 272 abuts the barrel flange 116, while the opposing surfaces 266, 278 of the barb 262 and the collar 268 also abut. In this fashion, the closure 206 is secured indirectly to the barrel flange 116.

In use, the collar 268 may be positioned on the barrel 102 first, with the collar 268 being advanced from the second end 118 to the first end 112, until the barrel flange 116 abuts the collar 268 and is received within the recess 272. At this point, the filter 224 may be disposed between the stopper 120 and the cap 222, and the cap 222 pressed downward towards the collar 268. The barbs 262 may deflect outwardly as the barbs 262 are moved through the apertures 276, until the head 264 of the barb 262 passes beyond the outer surface 278 of the collar 268. At this point, the barbs 262 move inwardly and the surfaces 266, 278 abut to hold the cap 222 to the collar 268, with the barrel flange 116, stopper 120 and filter 224 sandwiched between the cap 222 and the collar 268.

Figure 8A:
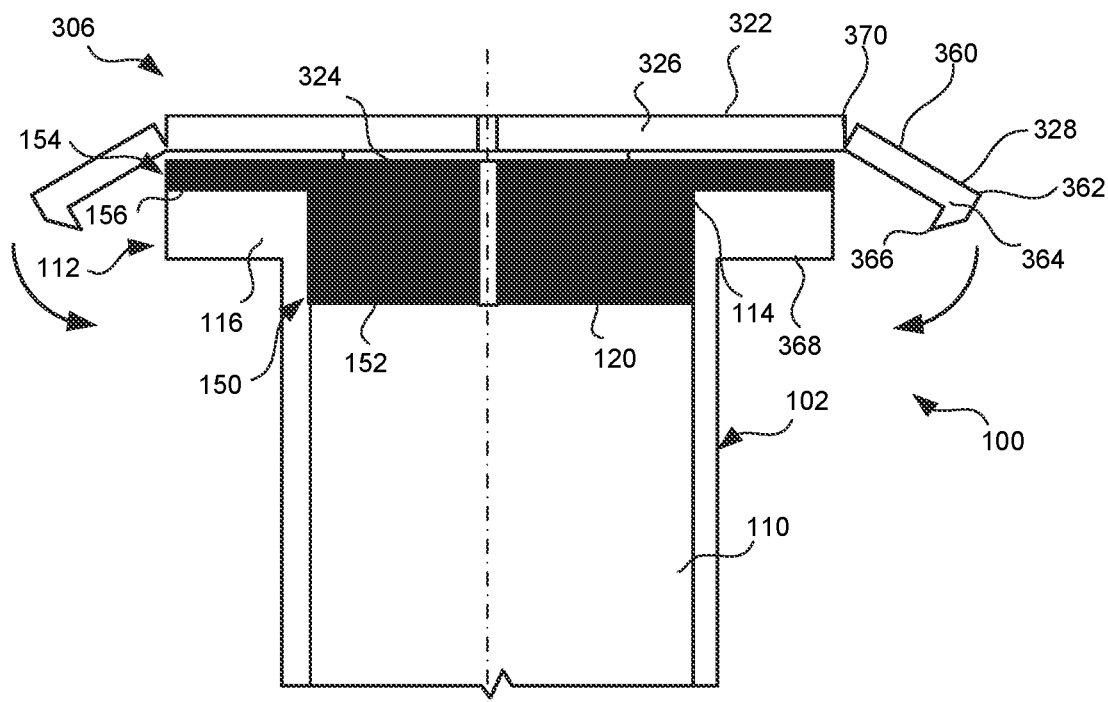
FIG. 8A is a partial, enlarged, cross-sectional view of a syringe with syringe closure according to a further embodiment, with a fastener disengaged from the barrel flange.
Figure 8B:
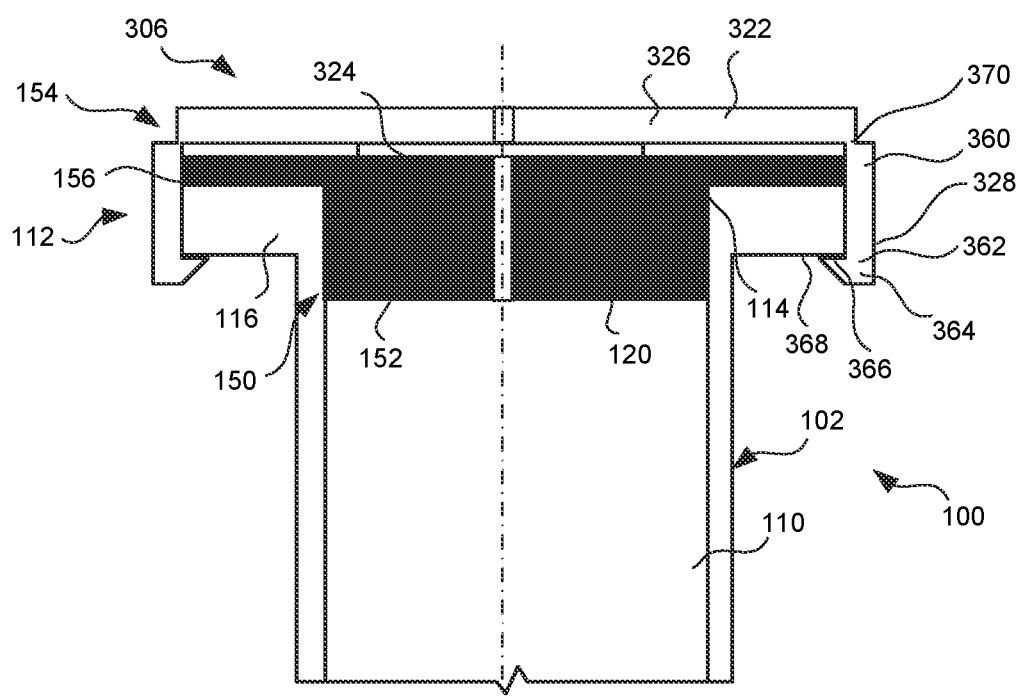
FIG. 8B is a partial, enlarged, cross-sectional view of the embodiment of FIG. 8A, with the fastener engaged with the barrel flange.

FIGS. 8A and 8B illustrated a vented closure 306 that is attached to the barrel 102 of the syringe 100 as the first end 112. The vented closure 306 includes a stopper 120, a cap 322, and a filter 324. As in the embodiment of FIGS. 1-5, the stopper 120 is disposed over and in the opening 114 in communication with the bore 110. The cap 322 includes a body 326 disposed over the stopper 120, and a fastener 328 engaged with the barrel flange 116. The filter 324 is illustrated as disposed between the stopper 120 and the cap 322.

The embodiment of FIGS. 8A and 8B is similar to that of the embodiment of FIGS. 7A and 7B in that the skirt 360 has a plurality of spaced barbs 362, each of the barbs 362 being supported separately about the periphery of the cap 322. Each of the barbs 362 has a head 364 with an inner surface 366, which has a function similar to the barbs in the embodiments discussed above. In the illustrated embodiment, the surface 366 abuts a surface 368 of the barrel flange 116; in a further embodiment, a collar may be used as in the embodiment of FIGS. 7A and 7B, and the surface 366 may abut a surface of the collar, which is itself in contact with the barrel flange 116.

A significant difference with the preceding embodiments is that the fastener 328 (and in particular the barbs 362) are connected to the body 326 of the cap 322 by a hinge 370. As illustrated, the hinge 370 is a living hinge, made of the material that forms the body 326 of the cap 322 and the skirt 360. According to other embodiments, the hinge 370 may be a separate structure as to at least one of the body 326 and the skirt 360, and joined to the body 326 and/or the skirt 360. The hinge 370 permits the fastener 328 to be spaced at a distance from the syringe 100 during the attachment of the closure 306 to the syringe 100.

In use, the filter 324 is disposed on the stopper 120, or according to certain embodiments the filter 324 is joined to the stopper 120, The cap 322 is then disposed over the stopper 120 and filter 324, as seen in FIG. 8A. The fasteners 328 may then be brought from a first position or state illustrated in FIG. 8A to a second position or state illustrated in FIG. 8B. As illustrated, in the first position, the barbs 362 are spaced radially outward of the body 326 of the cap 322, thereby limiting interference between the barbs 362 and the barrel flange 116 (or collar, in those embodiments where included) as the cap 322 is fitted onto the syringe. In the second position, the barbs 362 are brought into the second position where the surfaces 366, 368 abut to secure the cap 322 (and the closure 306) to the syringe 100.

Figure 9A:
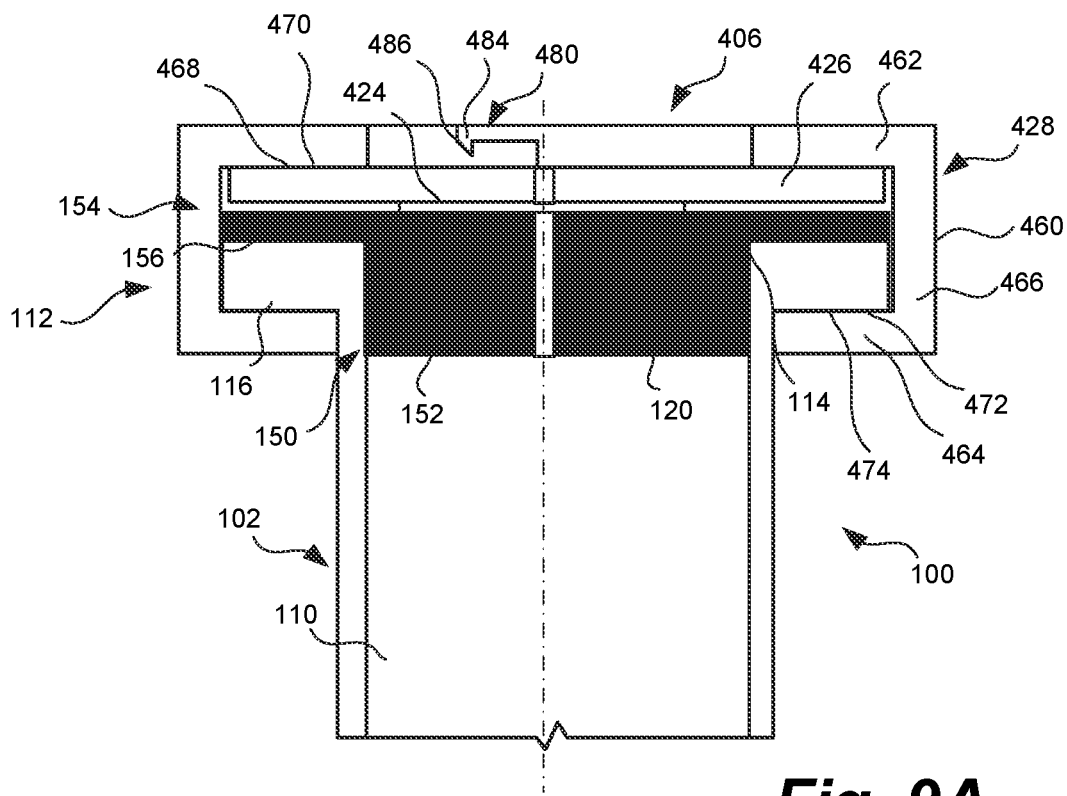
FIG. 9A is a partial, enlarged, cross-sectional view of a syringe with syringe closure according to yet another embodiment, with a fastener secured to the syringe.
Figure 9B:
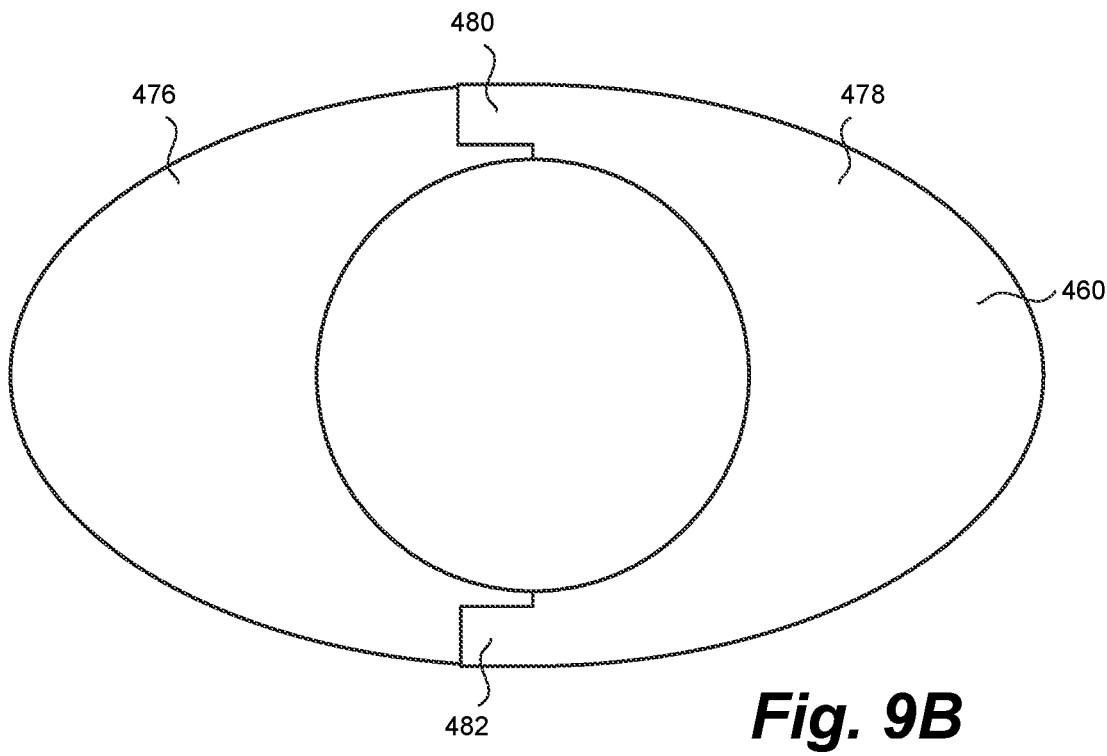
FIG. 9B is a plan view of the fastener of FIG. 9A, as connected to secure the closure to the syringe.

FIGS. 9A and 9B illustrate a vented closure 406 that is attached to the barrel 102 of the syringe 100 at the first end 112. The vented closure 406 includes a stopper 120, a cap 422, and a filter 424. As in the previous embodiments, the stopper 120 is disposed over and in the opening 114 in communication with the bore 110. The cap 422 includes a body 426 disposed over the stopper 120. Unlike the previous embodiments, the cap 422 has a fastener 428 that is a separate structure from the body 426 of the cap 422.

The fastener 428 is in the form of a C-shaped clamp 460, as viewed in the cross-section of FIG. 9A. It may be suggested that the clamp 460 performs the function of the skirt and the barb in the previous embodiments. The clamp 460 includes an upper section 462, a lower section 464, and a bridging section 466 that connects the upper section 462 to the lower section 464.

As installed in FIG. 9A, an inner surface 468 of the upper section 462 abuts an outer surface 470 of the body 426 of the cap 422. Similarly, an inner surface 472 of the lower section 464 abuts an outer surface 474 of the barrel flange 116. As a consequence, the body 426 of the cap 422, the filter 424, the stopper flange 156 and the barrel flange 116 are sandwiched between the opposed inner surfaces 468, 472 of the clamp 460 to secure the closure 406 to the syringe 100, and each of the components in place.

According to the illustrated embodiment, the clamp 460 has two mating halves 476, 478 (which may be referred to as a left half 476 and a right half 478 according to the orientation of the clamp 460 in FIG. 9B) which connect to each other to hold the clamp 460 in place on the syringe 100. To this end, one or more connectors may be disposed on the left half 476 or the right half 478 of the clamp 460, or mating portions of the connectors may be disposed on the left half 476 or the right half 478. The connectors hold the halves 476, 478 of the clamp 460 together to ensure that the closure 406 remains secured to the syringe 100.

As illustrated in FIG. 9B, the upper section 462 has two connectors 480, 482 disposed on opposite sides of the clamp 460 (which may also be opposite sides of the syringe 100). The lower section 464 may also have connectors (not shown) disposed on opposite sides of the clamp 460. While one arrangement has been illustrated, this not the only possible configuration for the connectors.

As best seen in FIG. 9A, each connector (e.g., the connector 480) may include a barb 484 and a recess 486. As illustrated, the barb 484 may be part of (joined to or integral with) the right half 478, while the recess 486 may be formed in the left half 476. This is an example of an embodiment of the connector where mating portions of the connectors may be disposed either on the left half 476 or the right half 478. The barb 484 may be received in the recess 486 such that complementary structures of the barb 484 and receive 486 mate, preventing the barb 484 from being removed or separated from the recess 486 without a particular amount of force being applied. This amount of force may be selected according to the normal operating conditions for the closure, and whether the fastener 428 is intended to be reversibly or irreversibly removable.

The connectors may be configured such that one half (e.g., the right half 478) has only the barbs 484, and the other half (e.g., the left half 476) has only the recesses configured to receive the barbs 484. Alternatively, the connectors of the upper section 462 may have barbs 484 on the right half 478 and recesses on the left half 476, while the lower section 464 has barbs on the left half 476 and recesses 486 on the right half 478. As a further alternative the connector 480 may have a barb 484 on the right half 478 and a recess 486 on the left half 476, while the connector 482 has a barb 484 on the left half 476 and a recess 486 on the right half 478. According to such an embodiment, the connectors on the lower section 464 may be the same as their counterparts on the upper section 462, or may be reversed.

It will also be recognized that while we have referred to the fastener 428 (and specifically the clamp 460) has having right and left halves 476, 478, this has been done for ease of explanation. The clamp 460 may have two relatively equal parts that are joined together to form the clamp 460, but it is not required that each part be exactly or approximately 50% of the overall structure. Further, while the clamp 460 has been illustrated as disposed about the entire periphery of the barrel flange 116 and stopper flange 156, this need not be the case with every instance of this embodiment of the closure 406.

In use, the filter 424 may be disposed over the stopper 120, and then the body 426 is disposed over the filter 424 and the stopper 120. A downward force may be applied to the body 426 to the filter 424 and stopper 120 as the halves 476 and 478 are advanced toward the syringe 100 from opposite sides of the syringe 100. The inner surface 468 of the upper section 462 of the clamp faces, and may even abut, the outer surface 470 of the body 426, and the inner surface 472 faces, and may even abut, the outer surface 474 of the barrel flange 116. The halves 476, 478 are advanced toward each other until the barbs 484 are advanced so far in the direction of the recess 486 that the barbs 484 and recess 486 mate, connecting the two halves 476, 478 of the clamp 460 together. In this position or state, the body 426, filter 424 and stopper 120, and barrel flange 116 are disposed between the opposing surfaces 468, 472 of the clamp 460.

It may also be possible to have a further embodiment, similar to that of FIGS. 9A and 9B, where the body 426 of the cap 422 is integrated into the upper section 462 of the clamp 460. For example, where the filter 424 is joined to or embedded in the stopper 120, the body 426 may be integrated into the supper section 462. In such a case, the opening in the center of the upper section 462 may be smaller than is illustrated in FIGS. 9A and 9B, as it is not necessary to apply force on the separate element of the cap 422 when advancing the halves 476, 478 toward each other.

The syringe with syringe closure according to the disclosed embodiments provides certain advantages relative to conventional syringes for use with pneumatic pumps. As mentioned above, the closure permits use of a pneumatic driver during filling, which limits or eliminates a potential source of contaminants as the air may be filtered easily. Further, the closure permits the syringe to be stored over a wide range of temperatures, while reducing the design burden on the plunger (particularly the plunger stopper) to provide the seal required during cryostorage. A syringe with incorporating such a closure can provide a ready-to-use delivery vessel, and one that is amenable to direct integration into instrumentation. The rigid nature of the container also may permit robotic instrumentation to facilitate connection for highly-scaled operations.

Thus, an improved syringe has been disclosed, in conjunction with an improved syringe closure. The description provided above, and the other aspects provided below, are intended for illustrative purposes, and are not intended to limit the scope of the disclosure to any particular method, system, apparatus or device described herein.

Other Aspects

Aspect 1. A syringe comprising:
a barrel with a bore, the barrel having an end with an opening in communication with the bore and a barrel flange disposed outwardly of the opening;
a plunger disposed in the bore, the plunger movable along the bore; and
a vented closure attached to the barrel at the end, the closure comprising a stopper, a cap and a filter,
the stopper disposed over and/or in the opening in communication with the bore,
the cap having a body disposed over the stopper, and a fastener engaged with the barrel flange,
the filter disposed between the stopper and the cap, or in at least one of the stopper and the cap.

Aspect 2. The syringe according to aspect 1, wherein the barrel flange comprises a collar disposed on the barrel at the end thereof.

Aspect 3. The syringe according to aspect 1 or 2, wherein the stopper comprises an elastomeric stopper with a plug disposed within the bore and a stopper flange depending from an end of the stopper outside the bore.

Aspect 4. The syringe according to aspect 3, wherein the cap secures the stopper flange between the body of the cap and the barrel flange.

Aspect 5. The syringe according to any one of aspects 1-4, wherein the fastener comprises a downwardly depending skirt having a barb that engages the barrel flange.

Aspect 6. The syringe according to aspect 5, wherein the barb has a surface that abuts a surface of the barrel flange to engage the barrel flange.

Aspect 7. The syringe according to aspect 5, wherein the closure comprises a collar that abuts the barrel flange, and the barb abuts a surface of the collar to engage the barrel flange.

Aspect 8. The syringe according to any one of aspects 5-7, wherein the fastener is attached to the body of the cap by a hinge.

Aspect 9. The syringe according to any one of aspects 1-4, wherein the fastener comprises a clamp having opposed inner surfaces, at least part of the stopper and the barrel flange disposed between the opposing inner surfaces of the clamp.

Aspect 10. The syringe according to aspect 9, wherein the clamp is disposed about the periphery of the syringe, and is divided into at least two parts that are connected with the at least part of the stopper and the barrel flange disposed between opposing inner surfaces of the clamp.

Aspect 11. The syringe according to aspect 9 or 10, wherein the body of the cap is separate from the clamp, and the body of the cap, the at least part of the stopper, and the barrel flange are disposed between the opposing inner surface of the clamp.

Aspect 12. The syringe according to any one of aspects 1-11, wherein the cap is configured to compress the stopper to create a hermetic seal in the bore.

Aspect 13. The syringe according to any one of the aspects 1-12, wherein the stopper and the body of the cap each have a through-lumen, the filter disposed between the through-lumen of the stopper and the through-lumen of the cap.

Aspect 14. The syringe according to aspect 13, wherein the through-lumen of the stopper and the through-lumen of the cap are aligned along a common longitudinal axis.

Aspect 15. The syringe according to any one of aspects 1-14, wherein the closure is removably attached to the barrel.

Aspect 16. The syringe according to aspect 15, further comprising a plunger handle, the plunger handle disposed through the opening and into the bore, the plunger handle attachable to the plunger to control movement of the plunger along the bore.

Aspect 17. The syringe according to any one of aspects 1-16, wherein the filter comprises 0.22 micron filter media.

Aspect 18. The syringe according to any one of aspects 1-17, wherein the barrel comprises cyclic olefin copolymer.

Aspect 19. The syringe according to any one of aspects 1-18, wherein the barrel has a second end opposite the end, the plunger moveable along the bore between the end and the second end, the second end comprising a tip in fluid communication with the bore.

Aspect 20. A processing set, comprising tubing and at least one syringe according to aspect 19, with the tip of the at least one syringe connected to the tubing.

Aspect 21. A processing system, comprising a pneumatic driver connected to the closure of a syringe according to any one of aspects 1-19.

The invention claimed is:
1. A syringe comprising:
a barrel with a bore, the barrel having an end with an opening in communication with the bore and a barrel flange disposed outwardly of the opening;
a plunger disposed in the bore, the plunger movable along the bore; and
a vented closure attached to the barrel at the end, the vented closure comprising a stopper, a cap and a filter,
the stopper comprising an elastomeric stopper having a first end comprising a plug disposed within the bore and having an outer surface in sealing engagement with the bore, and a second end disposed over the opening and a through lumen extending from the first end to the second end of the plug of the stopper, the stopper further comprising a stopper flange depending from the second end of the stopper outside the bore and against a first surface of the barrel flange, the cap having a body disposed over the stopper, a through lumen aligned along a common longitudinal axis with the through lumen of the plug of the stopper, and a fastener engaged with the barrel flange securing the stopper flange between the body of the cap and the barrel flange, the filter disposed between the stopper and the cap and between the respective through lumens of the stopper and the cap, wherein the fastener of the cap comprises a skirt having at least two sections spaced apart and depending downwardly from the body of the cap in snap fit engagement with a second surface of the barrel flange which is opposed to the first surface of the barrel flange.

2. The syringe according to claim 1, wherein the barrel flange comprises a collar disposed on the barrel at the end thereof.

3. The syringe according to claim 1, wherein the fastener further-comprises a plurality of barbs extending from the skirt which engage the barrel flange.

4. The syringe of claim 3, wherein each barb has a hook surface that abuts the second surface of the barrel flange when in snap fit engagement with the barrel flange.

5. The syringe according to claim 1, wherein the fastener is attached to the body of the cap by a hinge.

6. The syringe according to claim 1, wherein the cap is configured to compress the stopper to create a hermetic seal in the bore.

7. The syringe according to claim 1, wherein the vented closure is removably attached to the barrel.

8. The syringe according to claim 7, further comprising a plunger handle, and wherein when the removable vented closure is removed from the end of the barrel, the plunger handle is configured to be disposed through the opening and into the bore and attachable to the plunger to control movement of the plunger along the bore.

9. The syringe according to claim 1, wherein the filter comprises 0.22 micron filter media.

10. The syringe according to claim 1, wherein the barrel comprises cyclic olefin copolymer.

11. The syringe according to claim 1, wherein the barrel has a second end opposite the end, the plunger moveable along the bore between the end and the second end, the second end comprising a tip in fluid communication with the bore.

12. A processing set, comprising tubing and at least one syringe according to claim 11, with the tip of the at least one syringe connected to the tubing.

13. A processing system, comprising a pneumatic driver connected to the closure of a syringe according to claim 1.

* * * * *